US008029522B2

(12) United States Patent  
Ortiz et al.

(10) Patent No.: US 8,029,522 B2
(45) Date of Patent: *Oct. 4, 2011

(54) METHOD AND APPARATUS FOR SEALING A GASTRIC OPENING

(75) Inventors: Mark S. Ortiz, Milford, OH (US); Michael J. Stokes, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 692 days.

This patent is subject to a terminal disclaimer.

(21) Appl. No.: 11/197,516

(22) Filed: Aug. 5, 2005

(65) Prior Publication Data

US 2007/0078302 A1   Apr. 5, 2007

(51) Int. Cl.
*A61B 17/08*   (2006.01)
(52) U.S. Cl. .................... 606/155; 606/153; 606/213
(58) Field of Classification Search .............. 600/184, 600/115; 604/96.01; 606/213, 198, 139, 606/153, 155
See application file for complete search history.

(56) References Cited

U.S. PATENT DOCUMENTS

| 2,072,346 | A | * | 3/1937 | Smith ........................ 27/24.2 |
| 3,397,699 | A | * | 8/1968 | Kohl ........................... 604/105 |
| 4,643,184 | A | * | 2/1987 | Mobin-Uddin ............... 606/200 |
| 5,053,009 | A | * | 10/1991 | Herzberg ..................... 604/104 |
| 5,080,663 | A |   | 1/1992 | Mills et al. |
| 5,098,388 | A | * | 3/1992 | Kulkashi et al. ............. 604/158 |
| 5,171,259 | A | * | 12/1992 | Inoue ........................... 606/213 |
| 5,257,975 | A | * | 11/1993 | Foshee ........................ 604/105 |
| 5,376,101 | A |   | 12/1994 | Green et al. |
| 5,403,333 | A | * | 4/1995 | Kaster et al. ................. 606/151 |
| 5,437,681 | A |   | 8/1995 | Meade et al. |
| 5,449,356 | A | * | 9/1995 | Walbrink et al. ............. 606/49 |
| 5,454,365 | A | * | 10/1995 | Bonutti ........................ 600/204 |
| 5,462,558 | A |   | 10/1995 | Kolesa et al. |
| 5,514,159 | A |   | 5/1996 | Matula et al. |
| 5,540,705 | A |   | 7/1996 | Meade et al. |
| 5,549,565 | A | * | 8/1996 | Ryan et al. ................ 604/167.03 |
| 5,571,119 | A |   | 11/1996 | Atala |
| 5,685,826 | A | * | 11/1997 | Bonutti ........................ 600/204 |
| 5,709,693 | A |   | 1/1998 | Taylor |
| 5,713,910 | A |   | 2/1998 | Gordon et al. |
| 5,725,552 | A | * | 3/1998 | Kotula et al. ................ 606/213 |
| 5,797,920 | A | * | 8/1998 | Kim ............................ 606/108 |
| 5,814,071 | A |   | 9/1998 | McDevitt et al. |
| 5,823,956 | A | * | 10/1998 | Roth et al. ................... 600/374 |
| 5,843,088 | A | * | 12/1998 | Barra et al. .................. 606/108 |
| 5,853,422 | A | * | 12/1998 | Huebsch et al. ............. 606/213 |
| 5,855,565 | A | * | 1/1999 | Bar-Cohen et al. ......... 604/104 |
| 5,888,196 | A | * | 3/1999 | Bonutti ........................ 600/204 |

(Continued)

FOREIGN PATENT DOCUMENTS

EP   1545336   6/2005

(Continued)

*Primary Examiner* — Gary Jackson
*Assistant Examiner* — Erin Colello

(57) ABSTRACT

An anchorable cannula adapted for positioning within an opening formed in tissue includes a cannula body having a proximal portion and distal portion. The proximal portion and the distal portion are linked by a circumferential ring positioned therebetween. The proximal portion includes a series of foldable arms extending upwardly from the circumferential ring and ending at a circumferential seal ring formed at a free end of the proximal portion. The distal portion includes a series of foldable arms extending downwardly from the circumferential ring and ending at a circumferential seal ring formed at a free end of the distal portion.

6 Claims, 4 Drawing Sheets

U.S. PATENT DOCUMENTS

| | | | |
|---|---|---|---|
| 6,030,406 A * | 2/2000 | Davis et al. | 606/198 |
| 6,036,694 A | 3/2000 | Goble et al. | |
| 6,113,609 A * | 9/2000 | Adams | 606/139 |
| 6,312,446 B1 * | 11/2001 | Huebsch et al. | 606/213 |
| 6,346,074 B1 * | 2/2002 | Roth | 600/121 |
| 6,346,111 B1 | 2/2002 | Gordon et al. | |
| 6,379,368 B1 * | 4/2002 | Corcoran et al. | 606/153 |
| 6,443,962 B1 | 9/2002 | Gaber | |
| 6,447,533 B1 * | 9/2002 | Adams | 606/213 |
| 6,451,029 B1 * | 9/2002 | Yeatman | 606/139 |
| 6,454,778 B2 | 9/2002 | Kortenbach | |
| 6,485,496 B1 * | 11/2002 | Suyker et al. | 606/153 |
| 6,494,888 B1 | 12/2002 | Laufer et al. | |
| 6,506,196 B1 | 1/2003 | Laufer | |
| 6,543,456 B1 * | 4/2003 | Freeman | 128/898 |
| 6,558,400 B2 | 5/2003 | Deem et al. | |
| 6,632,227 B2 * | 10/2003 | Adams | 606/110 |
| 6,652,556 B1 * | 11/2003 | VanTassel et al. | 606/200 |
| 6,656,194 B1 | 12/2003 | Gannoe et al. | |
| 6,663,639 B1 | 12/2003 | Laufer et al. | |
| 6,669,674 B1 * | 12/2003 | Macoviak et al. | 604/264 |
| 6,669,713 B2 * | 12/2003 | Adams | 606/213 |
| 6,689,150 B1 * | 2/2004 | VanTassel et al. | 606/200 |
| 6,719,763 B2 | 4/2004 | Chung et al. | |
| 6,719,764 B1 | 4/2004 | Gellman et al. | |
| 6,746,460 B2 | 6/2004 | Gannoe et al. | |
| 6,755,843 B2 | 6/2004 | Chung et al. | |
| 6,773,440 B2 | 8/2004 | Gannoe et al. | |
| 6,835,200 B2 | 12/2004 | Laufer et al. | |
| 6,908,427 B2 | 6/2005 | Fleener et al. | |
| 6,923,819 B2 | 8/2005 | Meade et al. | |
| 7,004,949 B2 * | 2/2006 | Yencho et al. | 606/142 |
| 7,192,439 B2 * | 3/2007 | Khairkhahan et al. | 623/1.11 |
| 7,309,341 B2 * | 12/2007 | Ortiz et al. | 606/153 |
| 7,311,719 B2 * | 12/2007 | Bonutti | 606/192 |
| 7,452,363 B2 * | 11/2008 | Ortiz | 606/139 |
| 7,547,311 B2 * | 6/2009 | Ortiz | 606/142 |
| 7,621,950 B1 * | 11/2009 | Globerman et al. | 623/17.11 |
| 7,704,268 B2 * | 4/2010 | Chanduszko | 606/213 |
| 2001/0027317 A1 * | 10/2001 | Goble | 606/41 |
| 2001/0049497 A1 * | 12/2001 | Kalloo et al. | 604/164.01 |
| 2002/0107530 A1 | 8/2002 | Sauer et al. | |
| 2002/0128677 A1 * | 9/2002 | Duerig et al. | 606/198 |
| 2003/0032967 A1 * | 2/2003 | Park et al. | 606/153 |
| 2003/0083674 A1 | 5/2003 | Gibbens, III | |
| 2003/0109893 A1 * | 6/2003 | Vargas et al. | 606/153 |
| 2003/0149463 A1 * | 8/2003 | Solymar et al. | 623/1.1 |
| 2003/0171760 A1 | 9/2003 | Gambale | |
| 2003/0181924 A1 | 9/2003 | Yamamoto et al. | |
| 2003/0229296 A1 | 12/2003 | Ishikawa et al. | |
| 2003/0233104 A1 | 12/2003 | Gellman et al. | |
| 2003/0233108 A1 | 12/2003 | Gellman et al. | |
| 2003/0233142 A1 | 12/2003 | Morales et al. | |
| 2004/0034369 A1 | 2/2004 | Sauer et al. | |
| 2004/0044354 A1 | 3/2004 | Gannoe et al. | |
| 2004/0059350 A1 | 3/2004 | Gordon et al. | |
| 2004/0082963 A1 | 4/2004 | Gannoe et al. | |
| 2004/0088008 A1 | 5/2004 | Gannoe et al. | |
| 2004/0122473 A1 | 6/2004 | Ewers et al. | |
| 2004/0138682 A1 | 7/2004 | Onuki et al. | |
| 2004/0147941 A1 | 7/2004 | Takemoto et al. | |
| 2004/0147958 A1 | 7/2004 | Lam et al. | |
| 2004/0162568 A1 | 8/2004 | Saadat et al. | |
| 2004/0194790 A1 | 10/2004 | Laufer et al. | |
| 2004/0210243 A1 | 10/2004 | Gannoe et al. | |
| 2004/0260344 A1 | 12/2004 | Lyons et al. | |
| 2005/0015101 A1 | 1/2005 | Gibbens, III et al. | |
| 2005/0049634 A1 * | 3/2005 | Chopra | 606/213 |
| 2005/0055038 A1 | 3/2005 | Kelleher et al. | |
| 2005/0070926 A1 * | 3/2005 | Ortiz | 606/142 |
| 2005/0070931 A1 | 3/2005 | Li et al. | |
| 2005/0070935 A1 * | 3/2005 | Ortiz | 606/153 |
| 2005/0070939 A1 * | 3/2005 | Beaupre | 606/154 |
| 2005/0075653 A1 | 4/2005 | Saadat et al. | |
| 2006/0184234 A1 * | 8/2006 | Frazier et al. | 623/1.36 |
| 2006/0217748 A1 * | 9/2006 | Ortiz | 606/153 |
| 2007/0166852 A1 * | 7/2007 | Brown | 438/26 |

FOREIGN PATENT DOCUMENTS

| | | |
|---|---|---|
| EP | 1569709 | 9/2005 |
| WO | WO98/50104 | 11/1998 |
| WO | WO99/59666 | 11/1999 |
| WO | WO00/61012 | 10/2000 |
| WO | WO01/10312 | 2/2001 |
| WO | WO01/66001 | 9/2001 |
| WO | WO02/35980 | 5/2002 |
| WO | WO03/049619 | 6/2003 |

* cited by examiner

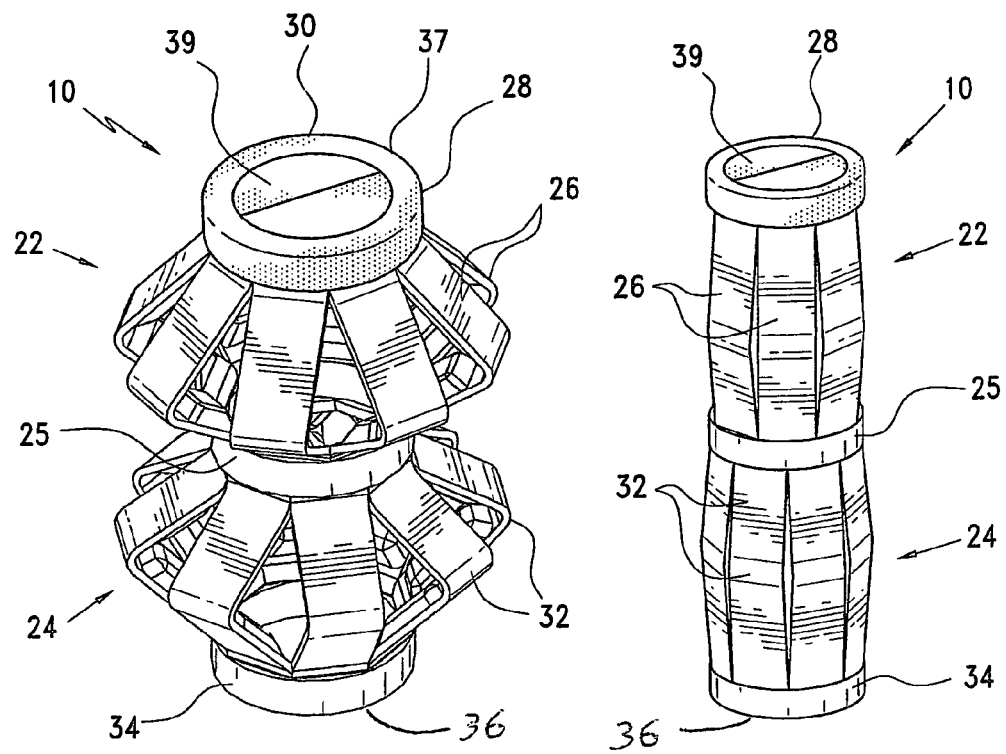
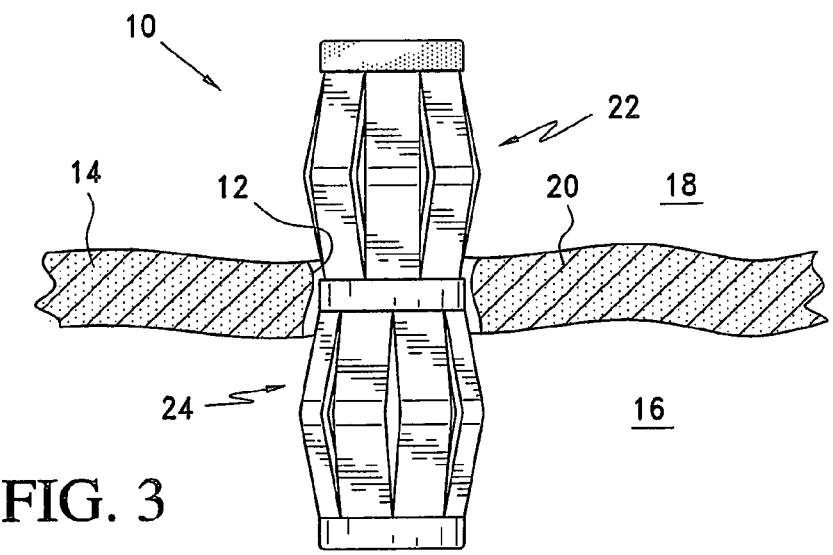
FIG. 1    FIG. 2
FIG. 3

METHOD AND APPARATUS FOR SEALING A GASTRIC OPENING

BACKGROUND OF THE INVENTION

1. Field of the Invention

The present invention relates to gastric surgery. More particularly, the invention relates to a method and apparatus for sealing a gastric opening in a manner facilitating transgastric surgery.

2. Description of the Prior Art

Morbid obesity is a serious medical condition. In fact, morbid obesity has become highly pervasive in the United States, as well as other countries, and the trend appears to be heading in a negative direction. Complications associated with morbid obesity include hypertension, diabetes, coronary artery disease, stroke, congestive heart failure, multiple orthopedic problems and pulmonary insufficiency with markedly decreased life expectancy. With this in mind, and as those skilled in the art will certainly appreciate, the monetary and physical costs associated with morbid obesity are substantial. In fact, it is estimated the costs relating to obesity are in excess of 100 billion dollars in the United States alone.

A variety of surgical procedures have been developed to treat obesity. Some of these procedures involve transgastric access to the stomach. However, these procedures have not been fully developed due the limited availability of tools necessary in performing transgastric procedures. In particular, transgastric procedures require a seal be positioned between the stomach and the peritoneal cavity, a mechanism for anchoring instruments to the gastric wall to allow the instruments to be triangulated so as to effectively work with the tissue and the ability to easily find the opening on reinsertion of the device. The present invention provides a device that accomplishes these three functions.

SUMMARY OF THE INVENTION

It is, therefore, an object of the present invention to provide an anchorable cannula adapted for positioning within an opening formed in tissue. The anchorable cannula includes a cannula body having a proximal portion and distal portion. The proximal portion and the distal portion are linked by a circumferential ring positioned therebetween. The proximal portion includes a series of foldable arms extending upwardly from the circumferential ring and ending at a ring formed at a free end of the proximal portion. The distal portion includes a series of foldable arms extending downwardly from the circumferential ring to and ending at a ring formed at a free end of the distal portion.

It is also an object of the present invention to provide a method for performing transgastric surgery. The method includes the steps of applying an anchorable cannula to a gastric wall and accessing the peritoneal cavity by passing surgical instruments through the stomach and anchorable cannula.

Other objects and advantages of the present invention will become apparent from the following detailed description when viewed in conjunction with the accompanying drawings, which set forth certain embodiments of the invention.

BRIEF DESCRIPTION OF THE DRAWINGS

FIG. 1 is a perspective view of the present anchorable cannula.

FIG. 2 is a perspective view of the anchorable cannula in its uncompressed state.

FIGS. 3, 4 and 5 are side views of the anchorable cannula showing the steps of deployment in accordance with the present invention.

DESCRIPTION OF THE PREFERRED EMBODIMENTS

Figure 4:
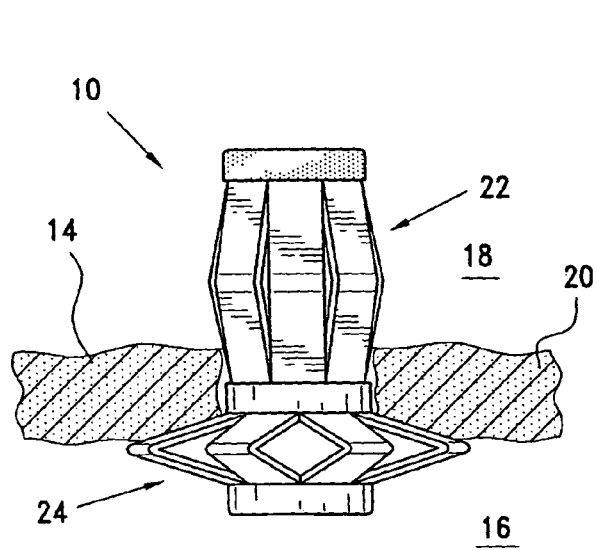
Figure 5:
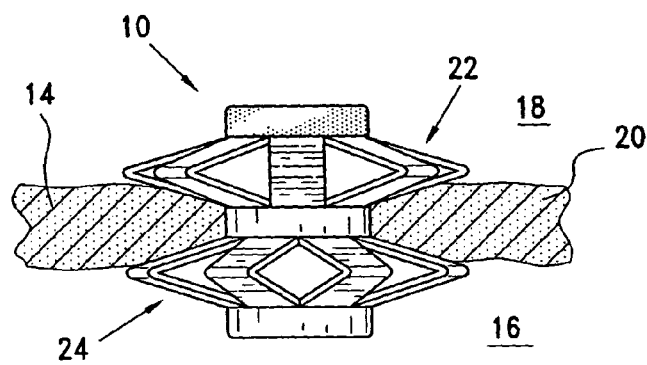

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as the basis for the claims and as a basis for teaching one skilled in the art how to make and/or use the invention.

With reference to the FIGS. 1 through 7 and 11, an anchorable cannula 10 is disclosed. A delivery device 100 for the anchorable cannula 10 is also disclosed. The anchorable cannula 10 is adapted for positioning within an opening 12 formed in the gastric wall 14 so as to define a readily usable opening therein. The anchorable cannula is particularly designed to prevent loss of pneumperitonium, to prevent leakage of gastric contents into the peritoneal cavity and to provide a repeatable path for instrument 17 insertion, in particular, endoscopic surgical instruments. The anchorable cannula 10 provides a seal between the stomach 16 and the peritoneal cavity 18, provides for the anchoring of instruments 17 to the gastric wall 14 to allow the instruments 17 to be triangulated so as to effectively work with tissue, allows for the ability to easily find the opening on reinsertion of a surgical instrument 17 and is readily extracted upon completion of the procedure.

More specifically, with the development of the present anchorable cannula 10 a repeatable instrument path is provided which facilitates the performance of the various transgastric procedures. With the anchorable cannula 10 properly secured to the gastric wall 14 in the manner discussed below in greater detail, a medical practitioner may insert and withdraw instruments through the anchorable cannula 10 for the performance of transgastric procedures without worrying that the path has moved or the position of the inserted instrument 17 has been altered.

As will be discussed below in greater detail, the present anchorable cannula 10 also provides a seal 37 and valve 39 between the stomach 16 and the peritoneal cavity 18. The provision of a seal 37 and valve 39 enhances the medical practitioners ability to perform transgastric procedures without worrying about the undesirable transfer of materials between the stomach 16 and the peritoneal cavity 18. The seal 37 and valve 39 also provide an anchoring mechanism for securely position surgical instruments 17 relative to the gastric wall 14 in a manner permitting triangulation of the surgical instruments 17 used during the procedures.

In general, the present anchorable cannula 10 provides for the performance of gastric surgery by applying the anchorable cannula 10 to a gastric wall 14 and accessing the peritoneal cavity 18 by passing surgical instruments 17 through the stomach 16 and anchorable cannula 10. In accordance with a preferred embodiment, a plurality of anchorable cannulas 10 are applied to the gastric wall 14 and a plurality of surgical instruments 17 are passed therethrough. The surgical instruments 17 are anchored to the anchorable cannulas 10 and the instruments 17 may be triangulated for the performance of a procedure.

The anchorable cannula 10 includes a proximal portion 22 and a distal portion 24. The proximal and distal portions 22, 24 are substantially similar and are linked by a circumferential ring 25 positioned therebetween. With regard to the proximal portion 22 of the anchorable cannula 10, it includes a series of foldable arms 26 extending upwardly from the circumferential ring 25 and ending at a circumferential seal ring 28 formed at the free end 30 of the proximal portion 22 of the anchorable cannula 10. Similarly, the distal portion 24 of the anchorable cannula 10 includes a series of foldable arms 32 extending downwardly from the circumferential ring 25 to a ring 34 at a free end 36 of the distal portion 24. This protects the tissue from trauma during repeated instrument insertion.

The seal ring 28 of the proximal portion 22 is provided with a rubber or silicone seal 37 that extends thereabout. The seal 37 assists in maintaining a barrier between the stomach and the peritoneal cavity for preventing leakage of organ contents. The seal ring 28 is further provided with a valve 39 selectively sealing the opening when instruments are not being passed therethrough. As those skilled in the art will certainly appreciate, the seal and valve may take a variety of forms without departing from the spirit of the present invention. Although the seal is disclosed in accordance with a preferred embodiment as being part of the seal ring at the proximal portion, it is contemplated the seal may be incorporated with the circumferential ring without departing from the spirit of the present invention.

As mentioned above, and with reference to FIG. 11, the present anchorable cannula 10 is designed for anchoring of surgical instruments 17 relative to the gastric wall 14 in a manner permitting triangulation of instruments 17 during transgastric procedures. With this in mind, the seal ring 28 of the proximal portion 22 is sized to provide for the selective engagement and anchoring of instruments 17 passing therethrough for relative positioning of the surgical instrument 17 in a manner permitting ready interaction of surgical instruments during a transgastric procedure.

When deployed, the series of foldable arms 26, 32 respectively making up the distal portion 24 and proximal portion 22 are collapsed toward the circumferential ring 25 thereby compressing upon the gastric wall 20 and securing the anchorable cannula 10 in position along the gastric wall 20. In accordance with a preferred embodiment of the present invention, the foldable arms 26, 32 are composed of a flexible material, for example, polyethylene or other plastics. The foldable arms 26, 32 prevent accidental displacement. Deployment of the anchorable cannula 10 and compression of the foldable arms 26, 32 will be discussed below in conjunction with the delivery device 100.

Figure 6:
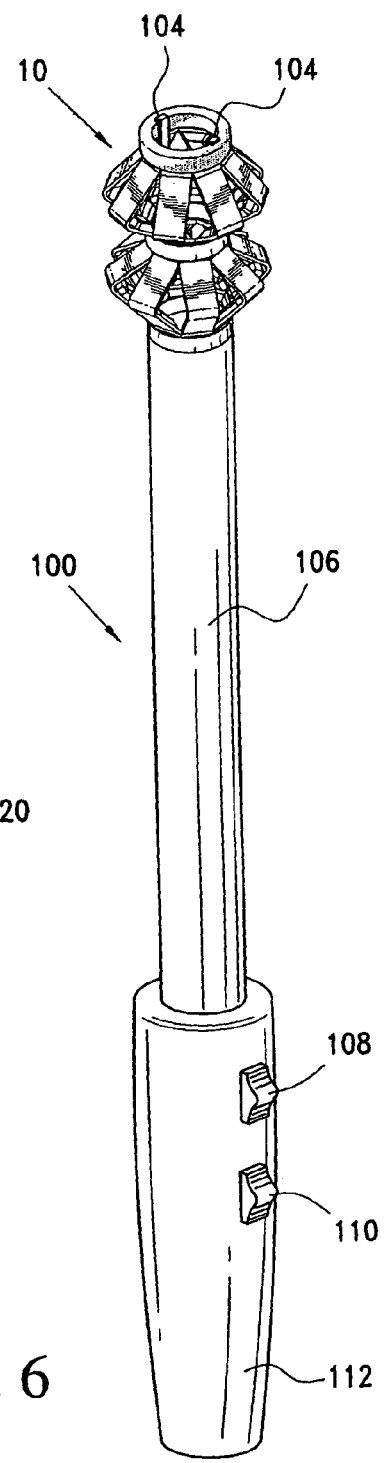
FIG. 6 is a side view of the delivery device used in accordance with the present invention.
Figure 7:
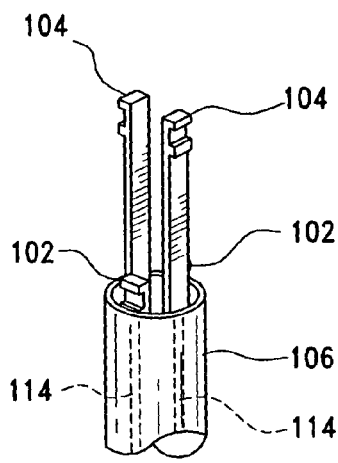
FIG. 7 is a detailed perspective view of the delivery device in accordance with the present invention.

Referring to FIGS. 6 and 7, a delivery device 100 for use in conjunction with the present anchorable cannula 10 is disclosed. The delivery device 100 includes distal applier fingers 102 and proximal applier fingers 104 extending from within a shaft 106. The distal applier fingers 102 engage the ring 34 at the free end 36 of the distal portion 34 of the anchorable cannula 10, while the proximal applier fingers 104 engage the seal ring 28 at the free end 30 of the proximal portion 22 of the anchorable cannula 10.

Movement of the distal applier fingers 102 and the proximal applier fingers 104 is achieved via finger actuation buttons 108, 110 at the proximal end 112 of the shaft 106. The finger actuation buttons 108, 110 allow for controlled movement of both the distal actuation fingers 102 and the proximal actuation fingers 104.

In practice, placement of an anchorable cannula 10 is accomplished by first perforating the gastric wall 20 with a standard endoscopic energy based cutting tool or needle knife. The small opening is dilated until the anchorable cannula 10 is inserted. The distal portion 24 of the anchorable cannula 10 is passed through the gastric wall 20 and tension is placed on the stomach wall 20 to ensure engagement of the distal portion 24 of the anchorable cannula 10 to the stomach wall 20. The distal portion 24 is tensioned by manipulating the distal applier fingers 102 to draw the circular ring 34 at the free end 36 of the distal portion 24 toward the circumferential ring 25 at the center of the anchorable cannula 10. By drawing the distal ring 34 toward the circumferential ring 25, the foldable arms 32 are folded outwardly and toward the gastric wall 20. While the distal portion 24 is compressed, the circumferential ring is held in position by the delivery instrument as discussed below in greater detail. The foldable arms 32, due to their material construction remain in this compressed configuration.

Similarly, the proximal portion 32 is deployed and latched into place. The proximal portion 22 is deployed in the same manner as the distal portion 24 with the exception that the proximal portion 22 is deployed via actuation of the proximal applier fingers 104.

Once the proximal and distal portions 22, 24 are fully drawn toward the circumferential ring 25 and are compressed with the gastric wall 20 therebetween, the delivery device 100 is removed, the seal 37 on the seal ring 28 of the proximal portion 22 deploys and the peritoneal cavity is isolated from the stomach. Deployment is achieved due to the elasticity of the seal 37 and valve 39 that causes them to "snap" into place when not spread by the applier. It is contemplated, however, that the seal may employ a spring loaded hinge valve used in deployment thereof.

Although movement of the distal and proximal applier fingers 102, 104 may be achieved by various mechanisms, cables 114 are utilized in accordance with the present invention to effectuate movement thereof. However, those skilled in the art will appreciate that other actuation mechanisms may be employed without departing from the spirit of the present invention.

Once properly installed, an ideal seal is provided. Although it is not essential that a leak proof seal be provided, the present anchorable cannula seals the stomach from the peritoneal cavity in an effective manner. As mentioned above, the seal ring 28 of the proximal portion 22 is sized to engage and anchor an instrument 17 passing therethrough for relative positioning of the surgical instrument 17 in a manner permitting ready interaction of surgical instruments during a transgastric procedure. The ability to anchor surgical instruments 17 relative to the stomach wall permits triangulation of the surgical instruments in a manner permits devices to work in opposition to each other. This enhances the effectiveness of the surgical instruments. For example, it may be placed in the pylorus or used in sealing off the GI tract to prevent gas distension.

Figure 8:
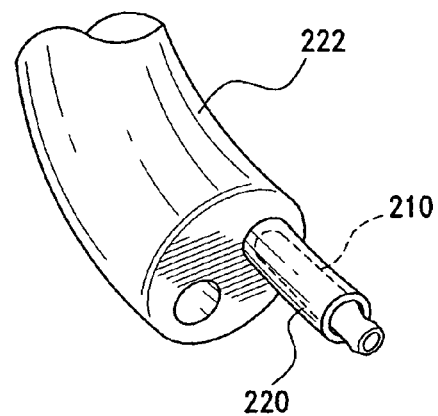
FIGS. 8, 9 and 10 are various views of an anchorable cannula in accordance with present invention.
Figure 9:
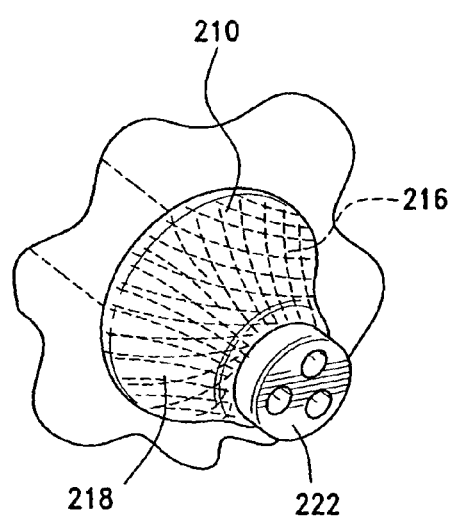
Figure 10:
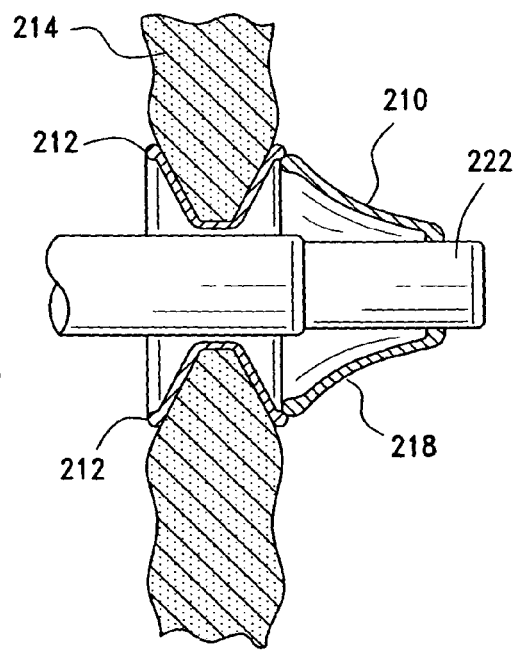
Figure 11:
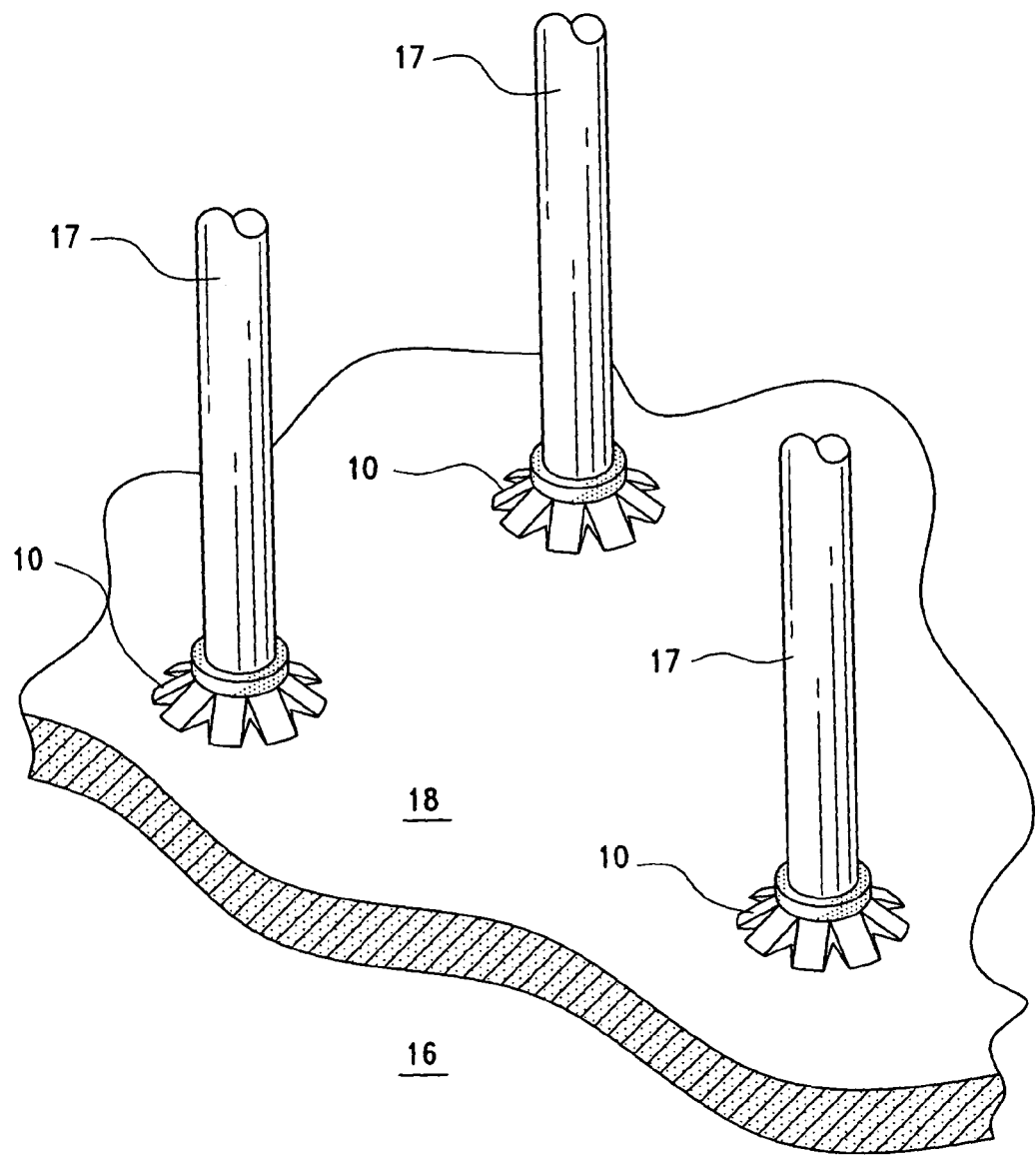
FIG. 11 is a perspective view of a plurality of anchorable cannulas in use with a plurality of instruments.

An alternate embodiment in accordance with the present invention is disclosed with reference to FIGS. 8, 9 and 10. This device 210 is based upon a stent-like construction which expands and collapses upon deployment. This device 210 is particularly adapted for dilation of the gastrotomy to enable passage of an endoscope into the peritoneal cavity. The device 210 is also adapted to provide a seal about an endoscope with respect to the stomach for the transgastric procedures.

As mentioned above, the device 210 has a substantially stent-like construction and is preferably manufactured from a Nitinol shape memory material which expands to a desired configuration upon deployment. It is contemplated the stent like structure of the present embodiment may be similar to that disclosed in U.S. Patent Application Publication Nos. 2003/0120292 and 2003/0032967, both entitled "ANASTOMOTIC DEVICE", which are incorporated herein by reference. In its expanded state, the device 210 includes distal fingers 212 shaped and dimensioned to engage the gastric wall 214 and a depending framework 216 shaped and dimensioned to create an opening for the controlled passage of instruments therethrough.

The device further includes a flexible membrane 218 which extends over the surface of the stent-like framework 216. The ends of the flexible membrane 218 are secured to the distal fingers 212. It is contemplated that the flexible membrane could also be manufactured so that it will naturally twist about its axis. The flexible membrane 218 and framework 216 are shaped and dimensioned such that the large diameter defined by the distal fingers 212 is adapted to engage the gastric wall 214, while the smaller opening is shaped and dimensioned for the passage of the endoscope therethrough.

In practice, the device 210 is stored within a tubular housing 220 attached to the endoscope 222. After a small gastrotomy is made with a needle knife, the tubular housing 220 is placed close to the opening and the device 210 is then deployed by pushing it from within the housing 220. When the distal fingers 212 of the device 210 deploy external to the gastric wall 214, the remainder of the device 210 deploys to fill the opening. The flexible membrane 218 covets the device 210 to form a highly functional sealing surface.

It is contemplated the functionality may be enhanced by varying the device disclosed in accordance with preferred embodiments of the present invention. For example, it could be made optically clear so that one could examine the tissue layers as the device is inserted or a stopcock could be attached thereto for instilling air into the peritoneal cavity. The device may also incorporate a cutting element at the distal end of the scope. In addition, the obturator may also serve as a closure device after the part is removed therefrom.

While the preferred embodiments have been shown and described, it will be understood that there is no intent to limit the invention by such disclosure, but rather, is intended to cover all modifications and alternate constructions falling within the spirit and scope of the invention.

The invention claimed is:

1. Anchorable cannula adapted for positioning within an opening formed in tissue, comprising:
    a cannula body having a proximal portion and distal portion; the proximal portion and the distal portion are linked by a circumferential ring positioned therebetween; the proximal portion includes a series of foldable arms extending upwardly from the circumferential ring and ending at a ring formed at a free end of the proximal portion, wherein the ring of the proximal portion is provided with a seal and a valve; the distal portion includes a series of foldable arms extending downwardly from the circumferential ring to a free end of the distal portion consisting essentially of a ring formed at the free end of the distal portion; and
    a delivery device for delivering the cannula body to a desired location, the delivery device includes a shaft within which a distal applier finger and a proximal applier finger are positioned for movement relative thereto such that the distal applier finger and the proximal applier finger extend from within the shaft and are shaped and dimensioned for positioning within the shaft, wherein the distal applier finger is shaped and dimensioned to engage the ring at the free end of the distal portion and the proximal applier finger is shaped and dimensioned to engage the ring at the free end of the proximal portion of the anchorable cannula.

2. The anchorable cannula according to claim 1, wherein the arms of the proximal portion and the arms of the distal portion are composed of a flexible material.

3. The anchorable cannula according to claim 1, wherein the delivery device includes finger actuation buttons for actuating the proximal applier finger and distal applier finger.

4. The anchorable cannula according to claim 1, wherein the cannula body includes a substantially stent-like framework.

5. The anchorable cannula according to claim 4, wherein the cannula body is manufactured from a shape memory material which expands to a desired configuration upon deployment.

6. The anchorable cannula according to claim 5, further including a flexible membrane which extends over the surface of the stent-like framework.

* * * * *